United States Patent [19]

Clardy et al.

[11] Patent Number: 5,164,511
[45] Date of Patent: Nov. 17, 1992

[54] THIOIMIDEAZOLES USEFUL AS INTERMEDIATES FOR PREPARING THIAZINE

[75] Inventors: Jon C. Clardy, Ithaca, N.Y.; Yael Asscher, Mevaseret Zion, Israel

[73] Assignee: Cornell Research Foundation, Inc., Ithaca, N.Y.

[21] Appl. No.: 765,825

[22] Filed: Sep. 26, 1991

[51] Int. Cl.$^5$ ............................................ C07D 233/84
[52] U.S. Cl. .................................................. 548/322.5
[58] Field of Search .......................................... 548/337

[56] References Cited

U.S. PATENT DOCUMENTS 4,898,878 2/1990 Shapiro et al. .................... 514/386

OTHER PUBLICATIONS

Cordes, A. W., et al, Acta Cryst. C42, 508–509 (1986).
de Silva, E. D., et al, Tetrahedron Lett. 32 (24), 2707–2710 (1991).
Gieren, A., et al, J. Am. Chem. Soc., 101, 7277–7281 (1979).
Holler, T. P., et al, J. Org. Chem. 54, 4570–4575 (1989).
Kokosa, J. M., et al, J. Org. Chem. 48, 3605–3607 (1983).
Lipinski, C. A., et al, J. Med. Chem. 29, 2154–2163 (1986).
Palumbo, A., et al, Comp. Biochem Physiol, 78B, 81–83 (1984).
Russell, G. A., et al, J. Org. Chem 31, 2854–2858 (1966).
Spaltenstein, A., et al, J. Org. Chem. 52, 2977–2979 (1987).
Yinglin, H., et al, Synthesis, 615–618 (Jul. 1990).

*Primary Examiner*—Patricia L. Morris

[57] ABSTRACT

Novel thioimidazoles are 5-carboxyaldehyde-1-methyl-4-(phenylmethyl)thioimidazole and 5-(α-aminoacetyl)-1-methyl-4-(phenylmethyl)thioimidazole acid addition salt. The latter is prepared from the former by steps comprising Grignard addition to form 5-(1-hydroxyethyl)-1-methyl-4-(phenylmethyl)thioimidazole, oxidizing the hydroxy compound to form the corresponding ketone, brominating under acidic conditions to form the bromoacetyl derivative, converting the bromo in the bromoacetyl derivative to N,N-diformylamino and then hydrolyzing. The latter thioimidazole is an intermediate for forming 5-methylimidazo[4,5-e]-1,2-thiazin-4(5H)-one, that is neamphine, and for forming 3-chloro-(5-methylimidazo) [4,5-e]-1,2-thiazin-4(5H)-one, that is 3-chloroneamphine.

2 Claims, No Drawings

THIOIMIDEAZOLES USEFUL AS INTERMEDIATES FOR PREPARING THIAZINE

This invention was made in part with Government support under National Institutes of Health grant number CA24487; the Government has certain rights in the invention. Other financial support was provided by the New York Sea Grant.

TECHNICAL FIELD

This invention is directed to two 5-substituted-1-methyl-4-(phenylmethyl)thioimidazole intermediates, to the preparation of one of them from the other and to a novel thiazine prepared from one of them.

BACKGROUND OF THE INVENTION

The isolation of substantially pure 5-methylimidazo[4,5-e]-1,2-thiazin-4(5H)-one from the New Guinea sponge *Neamphius huxleyi* is reported in DeSilva, P. E., et al, J. Tetrahedron Lett. 32, 2707 (1991) and is the subject of U.S. Ser. No. 07/683,457. It has the structure

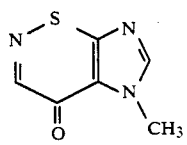

which also may be depicted as

It has been denoted neamphine.

Because screening testing of neamphine has indicated the potential for in vivo antineoplastic activity, synthesis thereof is desirable to increase the limited supply thereof available from the natural source to allow further definition of the biological activity and, in the event of determination of outstanding safety and efficacy, to provide a sufficient supply to satisfy demand.

SUMMARY OF THE INVENTION

The present invention involves the synthesis of a key intermediate 5-carboxyaldehyde-1-methyl-4-(phenylmethyl)thioimidazole and a further intermediate derived therefrom which is 5-($\alpha$-aminoacetyl)-1-methyl-4-(phenylmethyl)thioimidazole (acid addition salt form). The latter intermediate is readily converted to neamphine.

The latter intermediate is also readily converted to 3-chloro-(5-methylimidazo)[4,5-e]-1,2-thiazin-4(5H)-one which has been termed by the inventors herein as 3-chloroneamphine and which has the structure

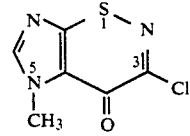

3-Chloroneamphine has antiviral, antineoplastic and immune system stimulatory functionality.

The intermediate 5-($\alpha$-aminoacetyl)-1-methyl-4-(phenylmethyl)thioimidazole acid addition salt is prepared from the intermediate 5-carboxyaldehyde-1-methyl-4-(phenylmethyl)thioimidazole by a method comprising the steps of (a) converting the 5-carboxyaldehyde group of 5-carboxyaldehyde-1-methyl-4-(phenylmethyl)thioimidazole to 5-(1-hydroxyethyl) by Grignard addition to form 5-(1-hydroxyethyl)-1-methyl-4-(phenylmethyl)thioimidazole, (b) oxidizing the hydroxy group of 5-(1-hydroxyethyl)-1-methyl-4-(phenylmethyl)thioimidazole, to form 5-acetyl-1-methyl-4-(phenylmethyl)thioimidazole, (c) brominating 5-acetyl-1-methyl-4-(phenylmethyl)thioimidazole under acidic conditions to form the hydrobromide salt of 5-bromoacetyl-1-methyl-4-(phenylmethyl)thioimidazole and converting to the free base, (d) reacting 5-bromoacetyl-1-methyl-4-(phenylmethyl)thioimidazole (free base form) with alkali metal diformylamide to convert the bromo in the bromoacetyl group to amine functionality to form 5-N,N-diformylaminoacetyl-1-methyl-4-(phenylmethyl)thioimidazole, (e) hydrolyzing 5-N,N-diformylaminoacetyl-1-methyl-4-(phenylmethyl)thioimidazole under mildly acidic conditions to form 5-($\alpha$-aminoacetyl)-1-methyl-4-(phenylmethyl)thioimidazole acid addition salt.

The 5-carboxyaldehyde-1-methyl-4-(phenylmethyl)thioimidazole intermediate which is a reactant for the above step (a) can be prepared by steps comprising condensing 1-methyl-4-(phenylmethyl)thioimidazole with formaldehyde under weakly acidic conditions to form 5-hydroxymethyl-1-methyl-4-(phenylmethyl)thioimidazole and oxidizing to form said reactant or by directly formylating 1-methyl-4-(phenylmethyl)thioimidazole to form said reactant.

DETAILED DESCRIPTION

The intermediate 5-carboxaldehyde-1-methyl-4-(phenylmethyl)thioimidazole has the structural formula

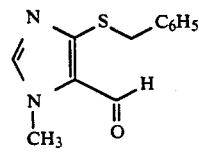

It is formed starting with 1-methyl-4-(phenylmethyl)thioimidazole which has the structural formula

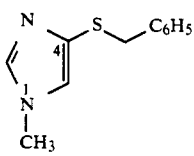

The starting material 1-methyl-4-(phenylmethyl)thioimidazole is prepared from 2-(N-formyl-N-methylamino)thionoacetamide by a condensation reaction to form the ring followed by addition of blocking group. A detailed preparation is set forth in Preparation 1 hereinafter. It involves suspension in dichloromethane and treatment of the 2-(N-formyl-N-methylamino)thionoacetamide with triethylamine and chlorotrimethylsilane and then after concentration, redissolving in ethanol and cooling, sequential treatment with sodium borohydride and benzyl bromide. The triethylamine and chlorotrimethylsilane treatments are readily carried out at room temperature over a time period of 3.5 to 5.5 hours. The cooling can be, for example, to 0° to 6° C. After benzyl bromide addition, the reaction mixture can be left, for example, at room temperature for 30 minutes up to 14 hours. Trimethylsilyl trifluoromethanesulfonate with reaction, for example, at 78° C., can be used in place of the chlorotrimethylsilane. The 2-(N-formyl-N-methylamino)thionoacetamide can be prepared as described in Shapiro et al U.S. Pat. No. 4,898,878 and in Holler, T. P., et al, J. Org. Chem. 54, 4570–4575 (1989); this preparation involves reacting N-(cyanomethyl)-N-methylformamide and hydrogen sulfide in triethylamine and ethanol at 25° C. until chromatography indicates the conversion is complete. The N-(cyanomethyl)-N-methylformamide is prepared by reacting formic acid treated with acetic anhydride with (cyanomethyl)methylamine in solution in dichloromethane at 0°–25° C. The (cyanomethyl)methylamine is prepared by reacting sodium cyanide, methylamine hydrochloride and 37% aqueous formaldehyde in water at 0° C.

As previously indicated, one method of preparing 5-carboxyaldehyde-1-methyl-4-(phenylmethyl)thioimidazole from 1-methyl-4-(phenylmethyl)thioimidazole comprises condensing 1-methyl-4-(phenylmethyl)thioimidazole with formaldehyde under weakly acidic conditions in a first step to form 5-hydroxymethyl-1-methyl-4-(phenylmethyl)thioimidazole and then oxidizing the formed primary alcohol in a second step to form the product. The first step is readily carried out by reacting using aqueous formaldehyde (e.g. 36.5% to 38% aqueous formaldehyde) in a buffered weakly acid medium, such as sodium formate/formic acid, preferably sodium acetate/acetic acid (pH ranging from about 5.5 to about 6.5) at 90° to 130° C., preferably at reflux over a time period ranging from about 2 to about 4 hours. The buffered weakly acid medium should be such as to protonate the formaldehyde but at most to partially protonate the imidazole moiety to enable an electrophilic attack on the imidazole ring. The second step of oxidizing the primary alcohol in the presence of a sensitive sulfide bond (i.e. without disturbing the sulfide bond) requires careful selection of oxidizing agent. Activated manganese dioxide is preferred for use as the oxidizing agent. Oxidizing agents which were functional but provided much lower yields than activated manganese dioxide included (a) 2,2,6,6-tetramethylpiperidinyl-1-oxy (TEMPO reagent) and CuCl, (b) $RuCl_2(PPh_3)_3$ and (c) pyridinium chlorochromate. This second step is readily carried out in a nonpolar or slightly polar solvent such as dichloromethane, acetonitrile or dioxane, preferably acetone, e.g. at a temperature ranging from room temperature to 45° C. for a time period ranging from 6 to 24 hours.

As previously indicated, another method for preparing 5-carboxyaldehyde-1-methyl-4-(phenylmethyl)thioimidazole is by directly formylating 1-methyl-4-(phenylmethyl)thioimidazole to form said product. This direct formylation is carried out using mild Vilsmeier-Haak conditions, i.e., phosphorus oxychloride and dimethylformamide e.g. at a temperature ranging from room temperature to 50° C. for a time period ranging from 3 to 24 hours under an inert atmosphere.

Turning now to the intermediate 5-(α-aminoacetyl)-1-methyl-4-(phenylmethyl)thioimidazole acid addition salt, it has the following structure where X is the anion of the acid addition salt portion

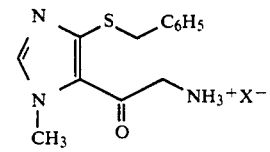

It is prepared from 5-carboxyaldehyde-1-methyl-4-(phenylmethyl)thioimidazole by a process comprising steps (a)–(e) as recited above. Provision in the acid salt form is important since the free base would dimerize on reaction to form neamphine.

We turn now to said steps (a)–(e).

In step (a), 5-carboxyaldehyde-1-methyl-4-(phenylmethyl)thioimidazole is converted to 5-(1-hydroxyethyl)-1-methyl-4-(phenylmethyl)thioimidazole which has the structure

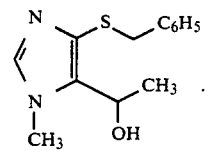

The Grignard reagent used in the Grignard addition is methyl magnesium halide, preferably methyl magnesium iodide. The reaction is carried out in an anhydrous slightly polar solvent, preferably diethyl ether, under an inert atmosphere, for example, at room temperature for a time period ranging from 2 to 6 hours. The reaction is stopped by addition of water, followed by optional basification, and then extraction.

In step (b), the 5-(1-hydroxyethyl)-1-methyl-4-(phenylmethyl)thioimidazole is converted to 5-acetyl-1-methyl-4-(phenylmethyl)thioimidazole which has the structure

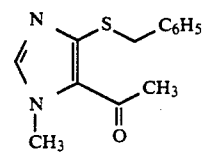

The oxidation of the hydroxy group to the ketone in this step can be carried out in moderately polar solvent, preferably acetone, at reflux temperature for a time period ranging from 4 to 24 hours. Preferably, the oxidizing agent is active manganese IV oxide. Other suitable oxidizing agents include, for example, (a) 2,2,6,6-tetramethylpiperidinyl-1-oxy (TEMPO reagent) and CuCl, (b) RuCl$_2$(PPh$_3$)$_3$ and (c) pyridinium chlorochromate.

In step (c) the 5-acetyl-1-methyl-4-(phenylmethyl)thioimidazole is converted to 5-bromoacetyl-1-methyl-4-(phenylmethyl)thioimidazole which has the structure

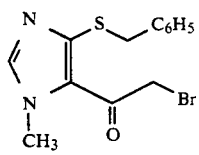

This is carried out in three substeps. In the first substep the 5-acetyl-1-methyl-4-(phenylmethyl)thioimidazole (free base form) is converted to the hydrobromide salt. This is carried out, for example, in a protic solvent, preferably methanol, by addition of aqueous HBr (e.g. 47 to 49% aqueous HBr) and reacting, for example, at room temperature for a time period ranging from 5 to 20 minutes. The hydrobromide salt produced is precipitated by addition of non-polar solvent, preferably ether. In the second substep the hydrobromide salt product of the first substep is converted to 5-bromoacetyl-1-methyl-4-(phenylmethyl)thioimidazole hydrobromide. This is carried out, for example, by dissolving the hydrobromide salt product of the first substep in aqueous HBr (e.g. 47 to 49% aqueous HBr) and then adding bromine and reacting at a temperature ranging from room temperature to 75° C. (gives multibromination and side products) for a time period typically ranging from 45 minutes to about 1 hour. In the third substep the free base form is obtained by reaction of the product of the second substep with neutralizing agent, preferably ethanolic solution of sodium hydroxide, which is readily carried out at room temperature for a time period ranging from 5 to 15 minutes.

In step (d) the 5-bromoacetyl-1-methyl-4-(phenylmethyl)thioimidazole is converted to 5-N,N-diformylaminoacetyl-1-methyl-4-(phenylmethyl)thioimidazole which has the structure

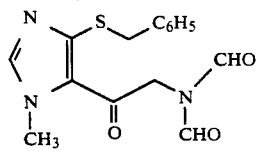

The reaction is carried out by reacting the product of step (c) with alkali metal diformylamide, preferably sodium diformylamide in anhydrous moderately polar solvent, preferably acetonitrile, at a temperature ranging from room temperature to 70° C. for a time period typically ranging from 4 to 24 hours.

In step (e) the 5-N,N-diformylaminoacetyl-1-methyl-4-(phenylmethyl)thioimidazole is converted to the 5-(α-aminoacetyl)-1-methyl-4-(phenylmethyl)thioimidazole acid addition salt. The reaction is carried out by dissolving the product of step (d) in aqueous acid in protic solvent, preferably in aqueous HCl in ethanol, for example, at room temperature for a time period typically ranging from 36 to 48 hours or at higher temperatures, e.g. 120° C., for shorter times, e.g. 30 minutes, with higher concentrations of HCl, e.g. 6N HCl. Preferably the aqueous acid is aqueous HCl and the hydrochloride salt is formed. Other aqueous acids can be used to form other acid salts. For example, aqueous HBr is useful to form the hydrobromide salt.

The intermediate 5-(α-aminoacetyl)-1-methyl-4-(phenylmethyl)thioimidazole acid addition salt (preferably the hydrochloride salt) is converted to neamphine by suspending said intermediate in dry nonpolar solvent, preferably dry chloroform, and reacting it with sulfuryl chloride, for example, at room temperature for a time period typically ranging from 12 to 24 hours followed by quenching with a neutralizing agent, preferably triethylamine.

The invention herein in one embodiment is directed at 3-chloro-(5-methylimidazo)[4,5-e]-1,2-thiazin-4(5H)-one, also referred to as 3-chloroneamphine. This is also prepared from the intermediate 5-(α-aminoacetyl)-1-methyl-4-(phenylmethyl)thioimidazole acid addition salt (preferably the hydrochloride salt) by reacting said intermediate suspended in dry non polar solvent (preferably dry chloroform) with chlorine in the form of chlorine saturated chloroform, for example, at room temperature for a time period ranging from 24 hours to 3 days and then quenching with neutralizing agent, preferably triethylamine.

The invention is illustrated by the following working examples.

In the working examples the following is the case. Unless otherwise specified commercial chemicals were used as received. When needed, dichloromethane was distilled under nitrogen from calcium hydride. Air or water sensitive reactions were performed under inert atmosphere or under calcium chloride drying tube. Thin layer chromatography (TLC) was carried out on Machery-Nagel precoated silica gel with fluorescent indicator. All flash and medium pressure liquid chromatography (MPLC) were carried out on silica gel 60 (70-230) mesh. Melting points were determined on Fisher-Jones melting point apparatus and are uncorrected. Infrared (IR) spectra were recorded on a Fourier Transform Mattson Polaris infrared spectrometer; only major or diagnostic peaks are noted. Proton and carbon nuclear magnetic resonance (NMR) spectra were determined on Bruker WM-300 and Varian XL-400 spectrometers and are reported in parts per million downfield relative to tetramethylsilane. Coupling constants are reported in Hz. Mass spectra electron impact, chemical ionization and high resolution were measured on an Associated Electronics Industries MS-902 spectrophotometer with a VG Micromass 2040 data reduction system; selected peaks are reported.

Preparation 1

The 1-methyl-4-(phenylmethyl)thioimidazole starting material for the intermediates was prepared as follows:

2-(N-formyl-N-methylamino)thionoacetamide (5 g, 37.8 mmol) was suspended in dichloromethane (115 mL) and triethylamine (34 mL). The resulting solution was mechanically stirred and treated at room temperature with chlorotrimethylsilane (23 mL). The stirring was continued for 5 hours. Then, the reaction mixture was concentrated under nitrogen stream. Anhydrous ethanol (100 mL) was added to the concentrated reaction mixture and the mixture was filtered from triethylammonium chloride. The filtrate was cooled to 0° C. and treated with sodium borohydride (0.7 g) followed by benzylbromide (5 mL) and the reaction mixture was left at room temperature overnight. The next day the reaction mixture was concentrated under reduced pressure and the crude product was purified by liquid chromatography using dichloromethane as eluent. The product afforded 3 g (39% yield) as a yellow oil. $^1$H NMR (200 MHz CDCl$_3$ δ 3.58 (s, 3H, NCH$_3$), 4.07 (s, 2H, SCH$_2$), 6.70 (s, 1H, 1m H-5), 7.2–7.3 (m, 5H, ArH), 7.44 (s, 1H, 1m H-2), $^{13}$C NMR (75 MHz, CDCl$_3$) δ 33.3, 39.9, 123.0, 126.8, 128.9, 133.6. 138.7 ppm; IR (neat) 3015, 2910, 1520, 1480, 1450, 1235, 690 cm$^{-1}$. The product recovered was 1-methyl-4-(phenylmethyl)thioimidazole.

EXAMPLE I

Preparation of 5-Carboxyaldehyde-1-methyl-4-(phenylmethyl)thioimidazole Via the Intermediate 5-Hydroxymethyl-1-methyl-4-(phenylmethyl)thioimidazole A solution of protected imidazole 1-methyl-4-(phenylmethyl)thioimidazole (4.5 g, 22 mmol), sodium acetate (36 g) and acetic acid (3.6 mL) in 37% aqueous formaldehyde was heated under reflux for 3.5 hours, with vigorous stirring. Then the reaction was cooled, diluted with water and basified with K$_2$CO$_3$ to pH 9–10. The aqueous solution was extracted with dichloromethane, dried and evaporated. The crude product was purified by liquid chromatography using dichloromethane as eluent to afford the product (2 g, 39% yield), mp 101° C.; $^1$H NMR δ 3.60 (s, 3H, NCH$_3$), 3.89 (s, 2H, SCH$_2$), 4.24 (s, 2H, CH2OH), 7.06–7.08 (m, 2H, ArH), 7.20–7.26 (m, 3H, ArH); 13C NMR (75 MHz, CDCl3) δ 32.0, 40.2, 53.2, 126.8, 128.1, 129.0, 130.5, 135.4, 138.7, 139.2 ppm; IR (KBr) 3300–2950 (OH), 1510, 1140, 850, 775, 700 cm$^{-1}$, LRMS (ei) m/z 234 (M+, 16%), 201 (M+-SH, 46), 143(53), 91 (C7H7+, 100), 65 (21). The product recovered was 5-hydroxymethyl-1-methyl-4-(phenylmethyl)thioimiadazole.

5-Hydroxymethyl-1-methyl-4-(phenylmethyl)thioimidazole (1.5 g, 6.4 mmol) was dissolved in acetone (75 mL), and activated manganese (IV) oxide (15 g) was added at once. The reaction was carried out under a calcium chloride drying tube, was vigorously stirred at room temperature for 7 hours, filtered, washed with acetone and evaporated. MPLC (silica) using dichloromethane as eluent afforded 1.15 g (77.4%) oil that solidifies upon standing at −20° C.: mp 57° C.; $^1$H NMR (300 MHz, CDCl$_3$) δ 3.88 (s, 3H,NCH$_3$), 4.30 (s, 2H, SCH$_2$), 7.27 (br s, 5H, ArH), 7.57 (s, 1H, 1m H-2), 9.63 (s,1H, CHO); $^{13}$C NMR (75 MHz, CDCl$_3$) δ 34.1, 37.6, 127.2, 128.4, 128.8; 129.3, 137.5, 142.9, 149.5, 178.7 (C=O); IR (KBr) 3100, 2850, 1670 (C=O), 1515, 1345, 1260, 1230, 800, 715, 690, 635 cm$^{-1}$. LRMS (ei) m/z 232 (M+, 11%), 199 (M+-SH, 66), 171 (43), 91 (C7H7+, 100), 70(17), 65(54), 42(65); HRMS (ei) calcd. 232.0670 obsd. 232.0670. The product formed was 5-carboxyaldehyde-1-methyl-4-(phenylmethyl)thioimidazole.

EXAMPLE II

Preparation of 5-Carboxyaldehyde-1-methyl-4-(phenylmethyl)thioimidazole Via the Direct Route Under argon and magnetic stirring, POCl$_3$ (0.4 mL, 4.3 mmol) was added to dimethylformamide (4 mL) in an ice salt bath. The reaction mixture was stirred for 10 min followed by the dropwise addition of 1-methyl-4-(phenylmethyl)thioimidazole (0.8 g, 3.4 mmol) in dimethylformamide (4 mL). The reaction continued 3 hours at room temperature followed by 3 hours at 50° C. Then it was poured on ice water, basified and extracted with dichloromethane (4×50 mL) and ethyl acetate (2×50 mL). The combined extracts were dried and evaporated. Purification by flash chromatography (petroleum ether:dichloromethane, 1:1) afforded 0.44 g (48.4%). The product was 5-carboxyaldehyde-1-methyl-4-(phenylmethyl)thioimidazole and was identical to the product synthesized in Example I.

EXAMPLE III

Preparation of 5-(α-Aminoacetyl)-1-methyl-4-(phenylmethyl)thioimidazole Hydrochloride 5-Carboxyaldehyde-1-methyl-4-(phenylmethyl)thioimidazole(7.9 g, 34 mmol) dissolved in anhydrous ether (300 mL) was added dropwise under argon and mechanical stirring to methylmagnesium iodide (14.5 mL of 3.0M solution in ether, 43.5 mmol) in ether (100 mL) during 10 min. During the addition a yellow precipitate appeared. The reaction was stirred for 1.5 hours at room temperature, cooled and decomposed by the addition of water followed by basification and extraction with dichloromethane. Evaporation of the dichloromethane afforded crude solid (7.9 g) which was purified by gradient flash chromatography (silica) starting with dichloromethane followed by 1% methanol in dichloromethane to provide 6.23 g (73.8%) of 5-(1-hydroxyethyl-1-methyl-4-(phenylmethyl)thioimidazole and 1.44 g of starting material :mp 115° C.; $^1$H NMR(400 MHz, CDCl$_3$) δ 1.15 (d, J=6.9 Hz, 3H, CH$_3$CH), 3.66 (s, 3H, NCH$_3$), 3.83, 3.85 (AB q, J=9.3 Hz, 2H, SCH$_2$), 4.80 (q, J=6.9 Hz, 1H, CHOH), 7.03 (d, J=7.5 Hz, 2H, ArH), 7.16–7.23 (m, 3H, ArH), 7.28 (s, 1H, 1m H-2); $^{13}$C NMR(100 MHz, CDCl$_3$) δ 21.4, 33.1, 40.1, 61.4, 126.7, 128.1, 129.0, 138.2, 139.9 139.1 ppm; IR(KBr) 3300–3000 (OH), 3070, 2950, 1510, 1455, 1250, 1175, 880, 690 cm$^{-1}$ LRMS (Cl, CH$_4$ m/z 249(MH+, 100%), 231 (MH+-H$_2$O, 93), 157(15), 91(C$_7$H$_7$+, 9), 89 (52), 61 (73); HRMS (ei) calcd. 248.0983 obsd. 248.0984.

5-(1-Hydroxyethyl)-1-methyl-4-(phenylmethyl)thioimidazole (6.2 g. 25 mmol) in acetone (310 ml) and active manganese IV oxide (62 g), under a calcium chloride drying tube, were mechanically stirred and refluxed for 4 hours. The reaction mixture was cooled, filtered, washed with dichloromethane and evaporated under reduced pressure to provide crude product. Purification by flash chromatography starting with dichloromethane followed by 1%, 2% and 10% methanol in dichloromethane provided 1.3 g of 5-acetyl-1-methyl-4-(phenylmethyl)thioimidazole (21%) and 3.6 g of starting material 5-(1-hydroxyethyl)-1-methyl-4-(phenylmethyl)thioimidazole (58%). The yield based on the starting material consumed is 50%; mp 62° C.; −H NMR(300 MHz, CDCl$_3$) δ 2.49 (s, 3H, CH$_3$CO), 3.86 (s, 3H, NCH$_3$), 4.45 (3, 2H, SCH$_2$), 7.26–7.37 (m, 5H, ArH), 7.49(s, 1H, 1m H-2); $^{13}$C NMR(75 MHz, CDCl$_3$) δ 30.4, 35.6, 37.2, 127.2, 128.1, 128.5, 129.0, 137.8, 142.0, 145.4, 188.4 (C=O) ppm; IR (CCl14) 3060, 2960, 1665 (C=O), 1550, 1515, 1250, 825, 730 cm$^{-1}$, LRMS (ei) m/z 246 (M+-SH, 100), 155 (23), 91 (C7H7+95), 81 (29), 42 (23); HRMS (ei) calc. 246.0827 obsd. 246.0826.

5-Acetyl-1-methyl-4-(phenylmethyl-thioimidazole (2.0 g, 8.1 mmol) dissolved in methanol (40 mL) and 48% aqueous hydrobromic acid (38 drops) was added.

The reaction was stirred at room temperature for 10 minutes followed by the addition of anhydrous ether (200 mL). White precipitate of the hydrobromide salt appeared. Filtration provided 1.94 g (73%) crude 5-acetyl-1-methyl-4-(phenylmethyl)thioimidazole hydrobromide that was used in the next step without further purification; mp 140°-145° C.; $^1$H NMR(300 MHz, $CDCl_3$) δ 2.50 (s, 3H, $CH_3CO$), 4.13(s, 3H, $NCH_3$), 4.67 (s, 2H, $SCH_2$), 7.26-7.33 (m, 5H, ArH), 9.69 (s, 1H, 1m H-2) ppm; IR (KBr) 3140, 3070, 2975, 2750-2200 ($NH^+$) 1670 (C=O), 1450, 1325, 1030 cm$^{-1}$.

5-Acetyl-1-methyl-4-(phenylmethyl)thioimidazole hydrobromide (1.0 g, 3.0 mmol) was dissolved in 48% aqueous hydrobromic acid (10 ml) and warmed to 60° C. Bromine (3.0 mmol, 155 μl, 480 mg) was added and stirring was continued at 60° C. for an hour. Then the reaction mixture was concentrated in vacuo. Recrystallization from isopropanol afforded 0.94 g (76%): mp 136° C., $^1$H NMR (300 MHz, $CDCl_3$) δ 4.17 (s, 3H, $NCH_3$), 4.34 (s,2H, $SCH_2$), 4.67 (s, 2H, $CH_2Br$), 7.26-7.33 (m, 5H, ArH), 10.04 (s, 1H, 1m H-2); $^{13}$C NMR (75 MHz, $CD_3OD$) δ 34.9, 38.5, 42.2, 129.3, 130.04, 130.09, 132.1, 132.3, 142.2, 183.5 (C=O)ppm.; IR (KBr) 3050, 2700-2400 ($NH^+$), 1675 (C=O), 1455, 1340, 1035, 710 cm$^{-1}$, LRMS (ei) m/z 326 ($M^+$, 4.3%), 324 ($M^+$, 4.2), 293 ($M^+$-SH, 3.7), 291 ($M^+$-SH, 3.77), 245 ($M^+$-Br, 64), 213 (8), 139 (11), 91 ($C_7H_7^+$, 100), 65 (10), 43 (24), 42 (16);HRMS (ei) calc. (for Br 79) 323.9932 obsd.323.9933. The product was 5-bromoacetyl-1-methyl-4-(phenymethyl)thioimidazole hydrobromide.

An ethanolic solution of NaOH (12.5 mL of 0.208 g NaOH in 25 mL absolute ethanol) was added to the bromoketone 5-bromoacetyl-1-methyl-4-(phenylmethyl)thioimidazole hydrobromide (1.04 g, 2.6 mmol). The reaction mixture was stirred for 5 minutes and chloroform (100 mL) was added. This solution was washed with water (30 mL). The aqueous phase was extracted with chloroform (50 mL) and the combined chloroform solutions were dried and evaporated in vacuo to afford 0.84 g. of the bromoketone free base.

The 0.84 g of the bromoketone free base was dissolved in dry acetonitrile (20 mL) and sodium diformylamide (487 mg. 5.13 mmol) was added. Processing was under a calcium chloride drying tube. The solution was stirred at room temperature for 24 hours. Then it was filtered, washed with acetonitrile and evaporated to afford crude 0.82 g. Purification by flash chromatography (silica) using dichloromethane as eluent followed by 0.5% methanol in dichloromethane provided the product 0.54 g (78%); mp 149°14 150° C.; $^1$H NMR(300 MHz $CDCl_3$) δ 3.86 (s, 3H, $NCH_3$), 4.50 (s, 2H, $SCH_2$), 4.90 (s, 2H, $COCH_2N$), 7.27-7.37 (m, 5H, ArH), 7.57 (s, 1H, 1m H-2), 8.99 (s, 2H, NCHO); $^{13}$C NMR (75 MHz, $CDCl_3$) δ 35.7, 37.7, 47.3, 126.6, 128.6, 129.0, 137.2, 143.0, 146.5, 163.1 (NCHO), 180.8 (ArC=O)ppm; IR ($CCl_4$) 3030, 2870, 1675 (C=O), 1660 (C=O), 1515, 1455, 1250, 1150, 990, 960, 810 cm$^{-1}$, LRMS (ei) m/z 317 ($M^+$, 51%), 284 $M^+$-SH, 21), 231 (23), 153 (15), 91 ($C_7H_7^+$, 100), 65 (29), 42 (22); HRMS (ei) calc. 317.0834 obsd. 317.0835. The product was 5-N,N-diformylaminoacetyl-1-methyl-4-(phenylmethyl)thioimidazole.

The 5-N,N-diformylaminoacetyl-1-methyl-4-(phenylmethyl)thioimidazole (375 mg, 1.18 mmol) was dissolved in freshly prepared 5% HCl/ethanol (5 mL) and the resulting solution was stirred at room temperature for 48 hours. Then, the solvent was evaporated under reduced pressure to afford the product as an hygroscopic glass-like solid. Recrystallization from isopropanol afforded 160 mg (45.5%).;mp 195° dec. $^1$H NMR (300 MHz $D_2O$) δ 3.90 (s, 3H, $NCH_3$), 4.19 (s, 2H, $SCH_2$), 4.28 (s, 2H, $COCH_2N$), 7.18-7.21 (m, 2H, ArH), 7.34-7.36 (m, 3H, ArH), 8.24(s, 1H, 1m H-2); $^{13}$C NMR (75 MHz, $D_2O$) δ 36.9 ($NCH_3$),40.1 ($SCH_2$), 47.4 ($COCH_2N$) 128.5, 129.4, 129.5, 130.1, 137.9, 144.7, 183.8 (C=O) ppm IR (KBr) 3200-2550 ($NH^+$), 1635 (C=O), 1505, 1465, 1270, 945, 700 cm$^{-1}$; LRMS (ei) m/z 261 ($M^+$, 56%), 203 (40), 199 (41), 171 (39), 170 (26), 91 ($C_7H_7^+$, 100) HRMS calc. 261. 0936 obsd. 261.0935. The product was 4-(α-aminoacetyl)-1-methyl-4-(phenylmethyl)thioimidazole hydrochloride.

EXAMPLE IV

Preparation of Neamphine from 5-(α-Aminoacetyl)-1-Methyl-4-(phenylmethyl)thioimidazole Hydrochloride 5-(α-Aminoacetyl)-1-methyl-4-(phenylmethyl)thioimidazole hydrochloride (45 mg) suspended in dry chloroform (5 mL) was magnetically stirred while sulfuryl chloride (15 μl, 0.2 mmol) was added through a septum. The reaction was stirred at room temperature overnight. The next day TLC revealed benzyl chloride. The reaction mixture was evaporated and hexane (5 mL) was added, stirred for 5 minutes and decanted. Dry chloroform was added to the solid followed by triethylamine (0.5 mL). The solid dissolved and red color appeared. After stirring was carried out for 10 minutes the reaction mixture was evaporated and purified by liquid chromatography (silica) starting with hexane:dichloromethane (1:1) followed by hexane:dichloromethane (1:2) to afford the product as colorless solid. 3 mg (12%). $^1$H NMR (300 MHz, $CDCl_3$) δ 4.21 (s, 3H, $NCH_3$), 7.86 (s, 1H), 8.65 (s, 1H) $^{13}$C NMR (100 MHz, $CDCl_3$) δ 34.7 ($NCH_3$), 126.6, 143.7 (1m C-2), 155.8, 158.1 (thiazine C-3), 167.3 (C=O) ppm IR (KBr) 3090, 1625 (C=O), 1515, 1470, 1390, 1355, 1270, 1210 cm$^{-1}$ LRMS (ei) m/z 167 ($M^+$, 100%), 140 ($M^+$-HCN, 52), 85 (51), 70 (930). HRMS (ei) calc. 167.0153 obsd 167.0152. The product was neamphine.

EXAMPLE V

Preparation of 3-chloroneamphine from 5-(α-Aminoacetyl)-1-methyl-4-(phenylmethyl)thioimidazole Hydrochloride 5-(α-Aminoacetyl)-1-methyl-4-(phenylmethyl)thioimidazole hydrochloride (45 mg) was suspended in dry chloroform (3 mL) and chlorine saturated chloroform (5 mL) was added. The reaction mixture was stirred at room temperature in a closed flask for 2 days. After 2 days more (2 mL) chlorine saturated chloroform was added and stirring was continued for another day. Then excess triethylamine was added and stirring was continued for 30 minutes. During that time the solid dissolved and red color appeared. Liquid chromatography on silica using dichloromethane as eluent afforded 5.5 mg of a colorless solid (13%). $^1$H NMR (300 MHz, $CDCl_3$) δ 4.20 (s, 3H, $NCH_3$), 7.88 (s, 1H, 1m H-2); $^{13}$C NMR (100 MHz, $CDCl_3$) δ 34.9 ($NCH_3$, 126.7, 144.9 (1m C-2), 151.3, 156.3, 161.3 (C=O); IR (KBr) 3080, 3000, 2975, 1620 (C=O), 1520, 1380, 1270, 1220, 1110 cm$^{-1}$; LRMS (ei) m/z 203 ($M^+$, 23.9%), 201 ($M^+$, 63.9), 140 (100), 85 (66). HRMS (ei) calc (for Cl 37) 202.9734 obsd. 202.9736. The product was 3-chloroneamphine. The effective dose for inhibiting L1210/c2 murine leukemia cells in vitro testing according to National Cancer Institute Protocol as set forth in NIH Publication No1 84-2635 is less than 10 μg/ml suggesting potential for in vivo antineoplastic activity.

Variations in the invention will be obvious to those skilled in the art. Therefore the invention is defined by the claims.

What is claimed is:

1. 5-Carboxyaldehyde-1-methyl-4-(phenylmethylthio)imidazole.
2. 5-(α-Aminoacetyl)-1-methyl-4-(phenylmethylthio)imidazole acid addition salt wherein the acid addition salt is formed at the aminoacetyl nitrogen and is selected from the group consisting of the hydrochloride salt and the hydrobromide salt.

* * * * *